United States Patent [19]

Stoltefuss et al.

[11] Patent Number: 4,822,798
[45] Date of Patent: Apr. 18, 1989

[54] CIRCULATION-ACTIVE 4-PHENYL-6-SUBSTITUTED DIHYDROPYRIMIDINES

[75] Inventors: Jürgen Stoltefuss; Horst Böshagen, both of Haan; Matthias Schramm, Cologne; Günter Thomas, Wuppertal, all of Fed. Rep. of Germany

[73] Assignee: Bayer Aktiengesellschaft, Leverkusen, Fed. Rep. of Germany

[21] Appl. No.: 526,931

[22] Filed: Aug. 26, 1983

[30] Foreign Application Priority Data

Sep. 18, 1982 [DE] Fed. Rep. of Germany ....... 3234684

[51] Int. Cl.[4] .................. A61K 31/505; C07D 239/20
[52] U.S. Cl. .................................... 514/255; 544/333; 544/335
[58] Field of Search ............... 424/251; 544/335, 333; 514/255

[56] References Cited

U.S. PATENT DOCUMENTS

3,905,970  9/1975  Bossert et al. ....................... 424/250

FOREIGN PATENT DOCUMENTS

2064096  7/1972  Netherlands.
2242787  3/1974  Netherlands.

OTHER PUBLICATIONS

Stoltefuss et al., Chem. Abst. 101:55110v (1984).
Khanina et al., Chem. Abst. 101=55048f (1984).
Chiba et al., Chem. Abst. 101=76112a (1984).
Budesinsky et al., Chem. Abst 93=132442a (1980).
Khanina et al., Chem. Abst. 92=163928x (1980).
Kumsars et al., Chem. Abst. 76:107917a (1972).
Zidermane et al., Chem. Abst. 75=47266e (1971).
Burger, Medicinal Chemistry, 2nd edition, 1960.
Merk Index, 9th edition, 6352 Nifedipine.
Grohe, Liebigs Ann. Chem. 1973, pp. 1025-1035.
Tachikawa et al., Chem. Pharm. Bull, vol. 30 (1982) pp. 564-568.
Breaux et al., J. Heterocyclic Chem. 18, (1981) p. 183.
Chem. Abst. vol. 77 (1972), 101656p, equiv to Dutch 2064096.
Chem. Abst. 1973, 92144g, Grohe et al.
Chem. Abst. vol. 80 (1974), 82869d, Shibuya et al.
Chem. Abst. vol. 96 (1982), 85501u, Goerlitzer et al.
Chem. Abst vol 95 (1981), 24972f, Breaux et al.
Arch. Pharm. Weinheim) 314, Gorlitzer and Buss, "2,4-Diaryl-6-methyl-1,2,3,4-tetrahydropyrimind-5-carbon-saureester", pp. 938, 949 (1981).

Primary Examiner—Donald G. Daus
Assistant Examiner—Cecilia Shen
Attorney, Agent, or Firm—Sprung Horn Kramer & Woods

[57] ABSTRACT

Circulatory system-active novel dihydropyrimidines of the formula

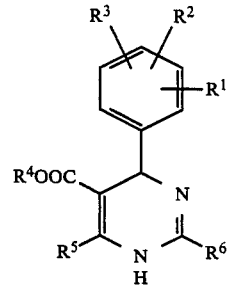

in which $R^1$ and $R^6$ are diverse organic radicals, and pharmacologically acceptable addition salts thereof.

10 Claims, No Drawings

CIRCULATION-ACTIVE 4-PHENYL-6-SUBSTITUTED DIHYDROPYRIMIDINES

The invention relates to new dihydropyrimidines, processes for their preparation and their use in medicaments, in particular in medicaments which influence the circulation.

It has already been disclosed that dihydropyrimidines can be obtained from benzamidine and α, β-unsaturated ketones (compare Silbersmith, J. Org. Chem. 27, 4090 (1982)). In contrast, it has also been disclosed that benzylidenemalonic acid esters give 3,4-dihydropyrid-2-ones with amidines (DE 2,242,787).

The invention relates to new dihydropyrimidines of the general formula (I)

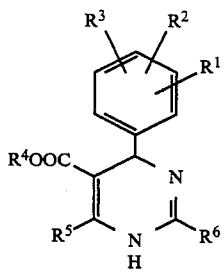

and the mesomeric form thereof Ia

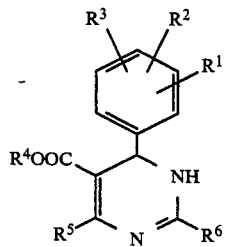

or an equilibrium between the two forms, in which
$R^1$, $R^2$ and $R^3$ are identical or different and represent hydrogen, an alkyl radical, halogen, halogenoalkyl, nitro, cyano, hydroxyl, alkoxy, aralkyl, amino, monoalkylamino or dialkylamino, or the radical

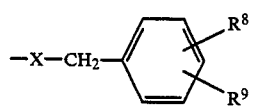

in which
X denotes O, S, SO or $SO_2$ and
$R^8$ and $R^9$ are identical or different and represent hydrogen, alkyl, halogen, alkoxy, nitro or $CF_3$;
$R^4$ represents hydrogen or a straight-chain, branched or cyclic, saturated or unsaturated hydrocarbon radical, which optionally contains one or two identical or different heterochain members from the group comprising O, CO, NH, N-alkyl, S and $SO_2$ and which is optionally substituted by halogen, nitro, cyano, hydroxyl, aryl, aralkyl, heteroaryl, amino, monoalkylamino or dialkylamino;
$R^5$ represents a straight-chain, branched or cyclic, saturated or unsaturated hydrocarbon radical, which is optionally substituted by halogen, hydroxyl, cyano, alkoxy, alkylthio, aryloxy, alkoxycarbonyl, amino, monoalkylamino, dialkylamino, aralkylamino or a 5-membered to 7-membered heterocyclic ring and
$R^6$ represents hydrogen, a straight-chain, branched or cyclic, saturated or unsaturated hydrocarbon moiety, which is optionally substituted by halogen, hydroxyl, cyano, nitro, alkoxy, alkylthio, aryloxy, alkoxycarbonyl, amino, monoalkylamino or dialkylamino, or an aralkyl, aryl or heterocyclic radical which is optionally substituted by halogen, hydroxyl, cyano, alkoxy, alkylthio, carboxyl, carbalkoxy, acyloxy, amino, nitro or mono- or di-alkylamino,
and their pharmacologically acceptable addition salts.

The new dihydropyrimidines of the general formula (I) or (Ia) according to the invention have valuable pharmaceutical properties. On the basis of their circulation-influencing action, they can be used as antihypertensive agents, as vasodilators, as cerebral therapeutics and as coronary therapeutics.

The compounds of the general formula (I) or (Ia) according to the invention can be prepared by a process in which (A) ylidene-β-keto esters of the general formula (II)

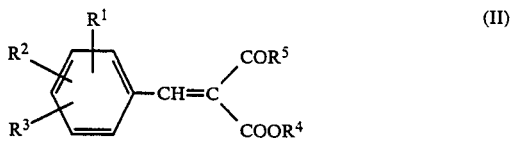

in which
$R^1$, $R^2$, $R^3$, $R^4$ and $R^5$ have the abovementioned meaning, are reacted with amidines of the general formula (III)

in which
$R^6$ has the abovementioned meaning, if appropriate in the presence of inert organic solvents, at temperatures between 20° and 150° C., with or without the addition of a base or acid, or (B) aldehydes of the general formula (IV)

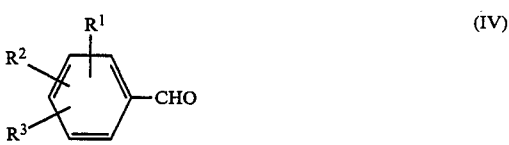

in which
$R^1$, $R^2$ and $R^3$ have the abovementioned meaning, are reacted with enaminocarboxylic acid esters of the general formula (V)

in which $R^4$ and $R^5$ have the abovementioned meaning, and amidines of the general formula (III), as described above, or (C) aldehydes of the general formula (IV)

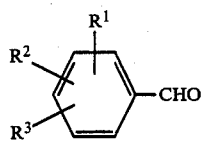

(IV)

in which $R^1$, $R^2$ and $R^3$ have the abovementioned meaning, are reacted with amidines of the formula (III)

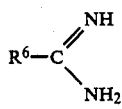

(III)

in which $R^6$ has the abovementioned meaning, and β-ketocarboxylic acid esters of the general formula (IV)

(VI)

in which $R^4$ and $R^5$ have the abovementioned meaning, if appropriate in the presence of inert organic solvents, with or without addition of a base or acid.

If methyl 3-chlorobenzylideneacetoacetate is reacted with acetamidine according to process variant (A), the reaction can be represented by the following equation:

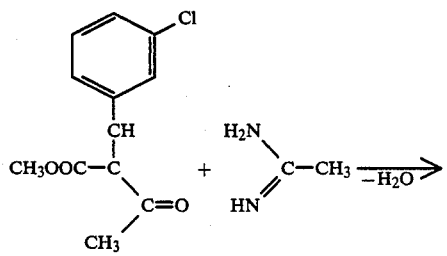

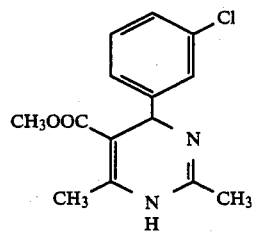

If 3-chlorobenzaldehyde is reacted with methyl β-aminocrotonate and benzamidine according to process variant (B), the reaction can be represented by the following equation:

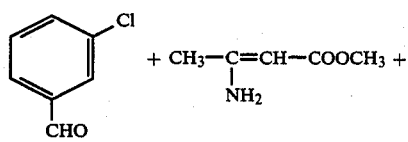

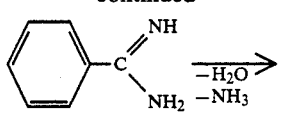

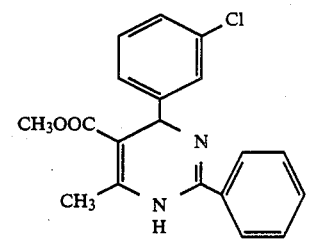

If 2-trifluoromethylbenzaldehyde is reacted with formamidine and ethyl acetoacetate according to process variant (C), the reaction can be represented by the following equation:

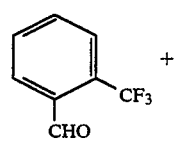

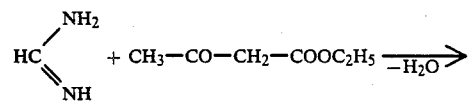

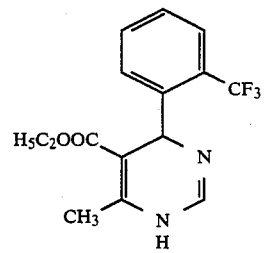

The ylidene-β-keto esters of the formula (II) used as starting substances can be prepared by methods which are known from the literature (compare G. Jones, "The Knoevenagel Condensation", in Org. Reactions, Volume XV, 204 et seq. (1967)).

The enaminocarboxylic acid esters (V) used as starting substances are known, or they can be prepared by methods which are known from the literature (compare A. C. Cope, J. Am. Chem. Soc. 67, 1017 (1945)).

The β-ketocarboxylic acid esters (VI) used as starting substances are known, or they can be prepared by methods which are known from the literature (for example D. Borrmann, "Umsetzung von Diketen mit Alkoholen, Phenolen und Mercaptanen" ("Reaction of diketene with alcohols, phenols and mercaptans"), in Houben-Weyl, Methoden der organischen Chemie (Methods of Organic Chemistry), Volume VII/4, 230 et seq. (1968); and Y. Oikawa, K. Sugano and O. Yonemitsu, J. Org. Chem. 43, 2087 (1978)).

The aldehydes (IV) used as starting substances are known, or they can be prepared by methods which are known from the literature (compare T. D. Harris and G. P. Roth, J. Org. Chem. 44, 146 (1979), German Offenlegungsschrift (German Published Specification)

2,165,260, July 1972, German Offenlegungsschrift (German Published Specification) 2,401,665, July 1974, Mijano et al., Chem. Abst. 59 (1963), 13 929 c, E. Adler and H. D. Becker, Chem. Scand. 15, 849. (1961) and E. P. Papadopoulos, M. Mardin and Ch. Issidoridis, J. Org. Chem. 31, 615 (1966), J. A. Chem. Soc. 78, 2543 (1956)).

The amidines (III) used as starting substances are known, or they can be prepared by methods which are known from the literature (compare Houben-Weyl, Methoden der organischen Chemie (Methods of Organic Chemistry), Volume 11/2, page 38 et seq. (1958); and R. L. Shoiner and F. W. Neumann, Chem. Reviews 35, 351 (1944)).

Possible diluents for all the process variants A, B and C are all the inert organic solvents. These include, preferably, alcohols, such as ethanol, methanol or isopropanol, ethers, such as dioxane, diethyl ether, tetrahydrofuran, glycol monomethyl ether or glycol dimethyl ether, or glacial acetic acid, dimethylformamide, dimethyl sulphoxide, acetonitrile, pyridine and hexamethylphosphoric acid triamide.

The reaction temperatures can be varied within a substantial range. In general, the reaction is carried out between 20° and 150° C., but preferably at the boiling point of the particular solvent.

The reaction can be carried out under normal pressure, but also under increased pressure. In general, it is carried out under normal pressure.

The reaction can be carried out with or without the addition of a base or acid, but it has been found that a reaction in the context of the invention preferably takes place in the presence of relatively weak acids, such as, for example, acetic acid or formic acid.

Dihydropyrimidines of the general formula (I) which are of particular interest are those in which $R^1$, $R^2$ and $R^3$ are identical or different and each represent hydrogen, alkyl with 1–4 carbon atoms, halogen, nitro, cyano, hydroxyl, amino, alkoxy with 1–4 carbon atoms, benzyl, monoalkylamino or dialkylamino with in each case 1–4 carbon atoms in the alkyl radicals or halogenoalkyl with 1–4 carbon atoms, or the radical

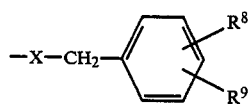

in which

X denotes O, S or $SO_2$ and $R^8$ and $R^9$ are identical or different and each represent hydrogen, nitro, trifluoromethyl, halogen or alkyl or alkoxy with in each case 1–4 carbon atoms, and $R^4$ represents hydrogen or a straight-chain, branched or cyclic alkyl or alkenyl radical, which optionally contains one or two identical or different heterochain members from the group comprising O, CO, NH, N-alkyl with 1–4 carbon atoms, S or $SO_2$ and which is optionally substituted by halogen, nitro, cyano, hydroxyl, phenyl, benzyl, pyridyl, amino or monoalkylamino or dialkylamino with in each case 1 to 4 carbon atoms in the alkyl radicals, and $R^5$ represents a straight-chain, branched or cyclic alkyl or alkenyl radical which has up to 10 carbon atoms and is optionally substituted by halogen, hydroxyl, cyano, amino, alkoxy, alkylthio, alkoxycarbonyl, monoalkylamino or dialkylamino with in each case 1–4 carbon atoms in the alkyl and alkoxy radicals, phenoxy, benzylamino or a 5-membered to 7-membered heterocyclic ring which contains one or two heteroatoms from the group comprising oxygen and nitrogen as ring members, and $R^6$ represents hydrogen, a straight-chain, branched or cyclic alkyl or alkenyl radical which has up to 10 carbon atoms and is optionally substituted by halogen, hydroxyl, cyano, nitro, amino, alkoxy, alkylthio, alkoxycarbonyl, monoalkylamino or dialkylamino with in each case 1–4 carbon atoms in the alkyl and alkoxy radicals or phenoxy, or represents a phenyl, naphthyl, benzyl or phenethyl radical, or a nitrogen-containing heteroaryl radical, the aryl radicals optionally being mono- or di-substituted by halogen, hydroxyl, cyano, amino, nitro, carboxyl or alkoxy, alkylthio, carbalkoxy, acyloxy, monoamino or dialkylamino with in each case up to 4 carbon atoms in the alkyl, alkoxy and acyl radicals, and their pharmacologically acceptable addition salts.

Compounds of the general formula (I) which are of very particular interest are those in which $R^1$, $R^2$ and $R^3$ are identical or different and represent hydrogen, alkyl with 1–4 carbon atoms, fluorine, chlorine, nitro, trifluoromethyl or the radical

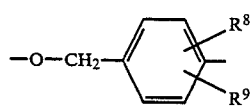

in which $R^8$ and $R^9$ are identical or different and represent hydrogen, alkyl with 1 to 4 carbon atoms, fluorine, chlorine, nitro or trifluoromethyl, $R^4$ and $R^5$ are identical or different and represent alkyl which has 1–6 carbon atoms, is optionally interrupted in the chain by an oxygen and is optionally substituted by fluorine, chlorine, cyano, nitro or phenyl, and $R^6$ represents hydrogen, alkyl with 1–4 carbon atoms, phenyl or pyridyl, and their pharmacologically acceptable addition salts.

The above preparation processes are only given for illustration, and the preparation of the compounds of the formula (I) or (Ia) is not limited to these processes, but any modification of these processes is applicable in the same way to the preparation of the compounds according to the invention.

The compounds according to the invention can exist in stereoisomeric forms, which either are mirror images (enantiomers) or are not mirror images (diastereomers), depending on the selection of the starting substances. The present invention relates both to the antipodes and to the racemic forms and the diastereomer mixtures. The racemic forms can be separated into the stereoisomerically pure constituents, as can the diastereomers, in a known manner (compare, for example, E. L. Eliel, Stereochemistry of Carbon Compounds, McGraw Hill, 1962).

The compounds of the general formula (I) or (Ia) display interesting biological actions. They have a broad and diverse pharmacological action spectrum and can be used as coronary agents and blood pressure agents. The following main actions may be mentioned specifically:

1. On parenteral, oral and perlingual administration, the compounds effect a distinct dilation of the coronary vessels. This action on the coronary vessels is intensified by a simultaneous nitrite-like effect of reducing the load on the heart.

They influence or modify cardiac metabolism in the sense of an energy saving.

2. The excitability of the stimulus formation and excitation conduction system within the heart is lowered, so that an antifibrillation action which can be demonstrated at therapeutic doses results.

3. The tone of the smooth muscle of the vessels is greatly reduced under the action of the compounds. This vascular-spasmolytic action can take place in the entire vascular system, or can manifest itself more or less isolated in circumscribed vascular regions (such as, for example, in the brain).

4. The compounds lower the blood pressure of normotonic and hypertonic animals and can thus be used as antihypertensive agents.

5. The compounds have powerfully muscular-spasmolytic actions, which manifest themselves on the smooth muscle of the stomach, the intestinal tract, the urogenital tract and the respiratory system.

6. The compounds have properties which lower the blood sugar content and have influence on the central nervous system.

The new active compounds can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example raw sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally in particular perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavor-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.01 to 10 mg/kg, preferably about 0.01 to 5 mg/kg, of body weight daily to achieve effective results, and in the case of oral administration, the dosage is about 0.1 to 20 mg/kg, preferably 0.5 to 5 mg/kg, of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it can suffice in some cases to manage with less than the above-mentioned minimum amount, while in other cases the upper limit mentioned must be exceeded. Where relatively large amounts are administered, it can be advisable to divide these into several individual administrations over the course of the day. The same dosage range is envisaged for administration in human medicine. The above statements also apply here in the general sense.

EXAMPLE 1

Ethyl 6-methyl-4-(2-nitrophenyl)-2-phenyl-1,4-dihydropyrimidine-5-carboxylate.

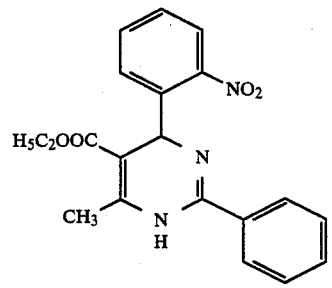

Process variant A 15.8 g (60 mmols) of ethyl 2-nitrobenzylidene-acetoacetate are boiled under reflux with 11.5 g (66 mmols) of benzamidine hydrochloride hydrate and 5.91 g (72 mmols) of anhydrous sodium acetate in 180 ml of ethanol for 18 hours. The mixture is cooled and concentrated. The evaporation residue obtained is taken up in a mixture of ethyl acetate, water and 100 ml of 1 N hydrochloric acid and the mixture is shaken vigorously and left to separate. The ethyl acetate phase is extracted once more with 100 ml of 1 N hydrochloric acid and the combined aqueous phases are extracted once by shaking with ether and then rendered alkaline with concentrated sodium hydroxide solution. The mixture is extracted twice with ethyl acetate and the combined ethyl acetate phases are washed with water, dried and concentrated. The resulting oil is stirred with a little cold acetonitrile; the crystals formed are filtered off with suction and washed with cold acetonitrile. 12.2 g (55.71% of theory) of a slightly yellow-colored product of melting point 102°–105° C. are obtained.

EXAMPLE 2

Methyl 2,6-dimethyl-4-(3-nitrophenyl)-1,4-dihydropyrimidine-5-carboxylate hydrochloride

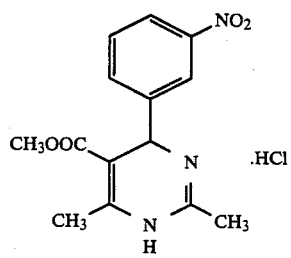

15 g (60 mmols) of methyl 3-nitrobenzylidene-acetoacetate are heated under reflux with 6.3 g (66 mmols) of acetamidine hydrochloride and 5.91 g (72 mmols) of anhydrous sodium acetate in 180 ml of ethanol for 18 hours. The mixture is concentrated. Ethyl acetate is added to the evaporation residue and the mixture is extracted with 2 100 ml portions of 1 N hydrochloric acid. The combined aqueous phases are extracted once by shaking with ether and then rendered alkaline with concentrated sodium hydroxide solution. The mixture is extracted twice with ethyl acetate and the combined ethyl acetate phases are washed with water, dried and concentrated. The resulting oily evaporation residue (6.6 g) is dissolved in methanol, and 23 ml of 1 N hydrochloric acid are added. The mixture is concentrated, the residue is concentrated again with ethanol and the resulting crystals are stirred with ethanol and filtered off with suction. 5.5 g of color less crystals of melting point 228° C., with decomposition, are obtained.

EXAMPLE 3

Ethyl 6-methyl-4-[2-(4-methylbenzyloxy)-phenyl]-2-phenyl-1,4-dihydropyrimidine-5-carboxylate hydrochloride

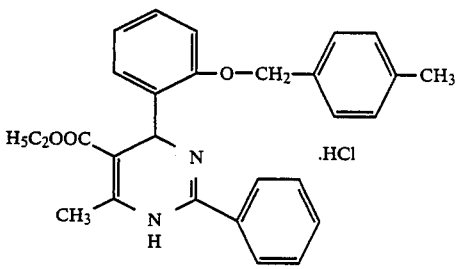

10.2 g (30 mmols) of ethyl 2-(4-methylbenzyloxy)-benzylideneacetoacetate are boiled under reflux with 5.75 g (33 mmols) of benzamidine hydrate hydrochloride and 2.95 g (36 mmols) of anhydrous sodium acetate in 90 ml of ethanol overnight. The mixture is concentrated; 100 ml of 1 N hydrochloric acid and 150 ml of ether are added to the evaporation residue and the mixture is stirred with a magnetic stirrer for four hours, whereupon the hydrochloride of the product precipitates. The hydrochloride is filtered off with suction, washed with water and ether and recrystallized from acetonitrile. 7.2 g (50.35% of theory) of an almost colorless product of melting point 223°–26° C., with decomposition, are obtained.

Analogously to process A, there were prepared (see following table).

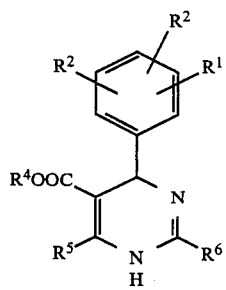

| Example No. | $R^1$ | $R^2$ | $R^3$ | $R^4$ | $R^5$ | $R^6$ | Melting Point °C. | Yield % |
|---|---|---|---|---|---|---|---|---|
| 4 | 3-Cl | | H | H | $CH_3$ | $CH_3$ | $CH_3$ | 211–13° C. decomposition Hydrochloride | 15.9 |
| 5 | 2-$NO_2$ | | H | H | $CH_3$ | $CH_3$ | $CH_3$ | 164 | 19 |
| 6 | 3-Cl | | H | H | $CH_3$ | $CH_3$ | H | 148–50 | 9.45 |
| 7 | 2-$NO_2$ | | H | H | $CH_3$ | $CH_3$ | H | 237 | 19.4 |
| 8 | 2-$CH_3$-⟨phenyl⟩-$CH_2$—O— | | H | H | $CH_3$ | $CH_3$ | H | 130–132 | 4.76 |

-continued

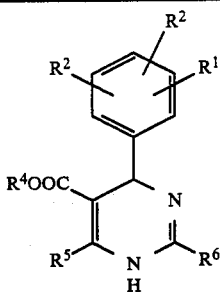

| Example No. | R¹ | R² | R³ | R⁴ | R⁵ | R⁶ | Melting Point °C. | Yield % |
|---|---|---|---|---|---|---|---|---|
| 9 | 2-CH₃-C₆H₄-CH₂-O— | H | H | C₂H₅ | CH₃ | CH₃ | 164–65 | 11.46 |
| 10 | 2-NO₂ | H | H | C₂H₅ | CH₃ | CH₃ | 146 | 23.1 |
| 11 | 2-NO₂ | H | H | C₂H₅ | CH₃ | H | 162 | 21.9 |
| 12 | 3-Cl | H | H | CH₃ | CH₃ | CH₃—CH₂—CH₂— | 131–32 | 4.85 |
| 13 | 3-NO₂ | H | H | CH₃ | CH₃ | CH₃—CH₂—CH₂— | 149–51 | 23.66 |
| 14 | 2-CF₃ | H | H | CH₃ | CH₃ | CH₃ | 134–54 | 59.71 |
| 15 | 2-CF₃ | H | H | CH₃ | CH₃ | C₆H₅ | 152–54 | 59.71 |
| 16 | 3-NO₂ | H | H | CH₃ | CH₃ | C₆H₅ | 243–45 HCl—Salt | 77.85 |
| 17 | 3-CH₃-C₆H₄-CH₂-O— | 4-CH₃ | H | CH₃ | CH₃ | C₆H₅ | 208–12 HCl—Salt | 22.31 |
| 18 | 2-CF₃ | H | H | CH₃ | CH₃ | H | 202–3 | 14.92 |

EXAMPLE 19

Methyl 4-(3-chlorophenyl)-6-methyl-2-phenyl-1,4-dihydropyrimidine-5-carboxylate hydrochloride

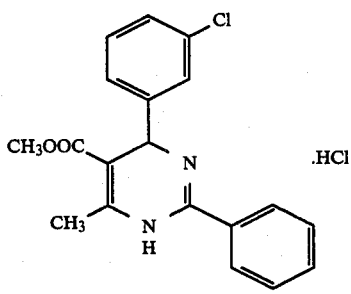

Process B 4.21 g (30 mmols) of 3-chlorobenzaldehyde are boiled under reflux with 3.45 g (30 mmols) of methyl aminocrotonate, 5.22 g (30 mmols) of benzamidine hydrochloride hydrate and 2.95 g (36 mmols) of anhydrous sodium acetate in 90 ml of ethanol for 16 hours. The mixture is cooled and concentrated. 75 ml of ethyl acetate and 50 ml of 1 N hydrochloric acid are added to the evaporation residue and the mixture is stirred with a magnetic stirrer. The salt which has precipitated is filtered off with suction, washed with ethyl acetate and dried. 2.7 g of slightly yellow-coloured crystals of melting point 237° C., with decomposition, are obtained.

The filtrate (ethyl acetate and aqueous hydrochloric acid) is left to separate, the ethyl acetate phase is extracted once by shaking with 50 ml of 1 N hydrochloric acid, the combined aqueous phases are shaken once with ether, separated off and rendered alkaline with concentrated sodium hydroxide solution. The mixture is extracted twice with ethyl acetate and the combined ethyl acetate phases are washed with water, dried and concentrated. The oily evaporation residue is dissolved in ethanol, 20 ml of 1 N hydrochloric acid are added and the mixture is concentrated. After concentrating the residue several times using acetonitrile, the resulting crystals are stirred with acetonitrile and filtered off with suction. 1.4 g of slightly yellow-colored crystals of melting point 237° C., with decomposition, are obtained, giving a total yield of 4.1 g (36.25% of theory).

Process C 4.21 g (30 mmols) of 3-chlorobenzaldehyde are boiled with 3.24 ml (30 mmols) of methyl acetoacetate, 5.22 g (30 mmols) of benzamidine hydrochloride hydrate and 2.95 ml (36 mmols) of anhydrous sodium acetate in 90 ml of ethanol for 16 hours. The mixture is cooled and concentrated. 50 ml of 1 N hydrochloric acid and 75 ml of ethyl acetate are added to the evaporation residue and the mixture is stirred with a magnetic stirrer, whereupon light yellow crystals precipitate. The crystals are filtered off with suction and washed with ethyl acetate. 4.4 g of slightly yellow-colored crystals of melting point 236°–38° C., with decomposition, are obtained. A further 1.3 g of the compound are obtained from the filtrate by the working up described in method B, whereupon the yield increases to 5.7 g (50.4% of theory).

EXAMPLE 20

Methyl 4-(2-chlorophenyl)-2,6-dimethyl-1,4-dihydro-pyrimidine-5-carboxylate

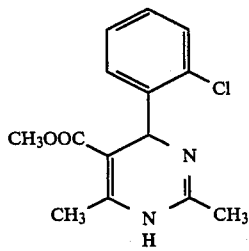

Process C 8.42 g (60 mmols) of 2-chlorobenzaldehyde are boiled with 6.48 ml (60 mmols) of methyl acetoacetate, 6.72 g (60 mmols) of acetamidine HCl and 5.91 g (72 mmols) of anhydrous sodium acetate in 180 ml of ethanol for 18 hours. The mixture is cooled and concentrated. 100 ml of 1N hydrochloric acid and ethyl acetate are added to the resulting evaporation residue and the mixture is shaken thoroughly. The mixture is left to separate, the ethyl acetate phase is extracted by shaking with 100 ml of 1 N hydrochloric acid and the combined aqueous phases are extracted once by shaking with ether and left to separate. The aqueous phase is rendered alkaline with concentrated sodium hydroxide solution and extracted twice by shaking with ethyl acetate. The combined ethyl acetate phases are washed with water, dried and concentrated. The crystalline evaporation residue is recrystallized from acetonitrile. 2.5 g of a slightly yellow substance of melting point 225°–27° C. are obtained.

The following compounds were prepared analogously to process C:

EXAMPLE 21

Methyl 2-(4-chlorophenyl)-4-(3-chlorophenyl)-6-methyl-1,4-dihydropyrimidine-5-carboxylate hydrochloride of melting point: 228° C., with decomposition.

EXAMPLE 22

Methyl 2-(3-chlorophenyl)-4-(2-chlorophenyl)-6-methyl-1,4-dihydropyrimidine-5-carboxylate hydrochloride of melting point: 219°–222° C., with decomposition.

EXAMPLE 23

Methyl 4-(2-chlorophenyl)-6-methyl-2-(4-pyridyl)-1,4-dihydropyrimidine-5-carboxylate of melting point: 150° C.

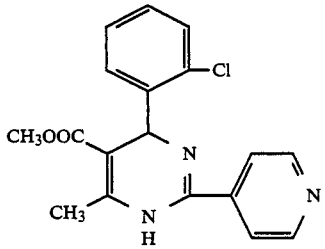

EXAMPLE 24

Methyl 4-(2-chlorophenyl)-6-methyl-2-(2-pyridyl)-1,4-dihydropyrimidine-5-carboxylate of melting point: 145° C.

In the following claims the more common formulas are given but they are intended to embrace the mesomeric forms as well as mixtures thereof.

It will be understood that the specification and examples are illustrative but not limitative of the present invention and that other embodiments within the spirit and scope of the invention will suggest themselves to those skilled in the art.

We claim:

1. A dihydropyrimidine of the formula

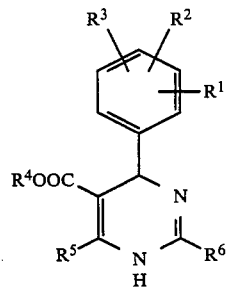

in which
$R^1$, $R^2$ and $R^3$ are identical or different and represent hydrogen, alkyl with 1–4 carbon atoms, fluorine, chlorine, nitro, trifluoromethyl or the group

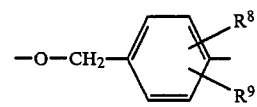

in which
$R^8$ and $R^9$ are identical or different and represent hydrogen, alkyl with 1–4 carbon atoms, fluorine, chlorine, nitro or trifluoromethyl,
$R^4$ and $R^5$ are identical or different and represent alkyl which has 1–6 carbon atoms, is optionally interrupted in the chain by an oxygen and is optionally substituted by fluorine, chlorine, cyano, nitro or phenyl, and
$R^6$ represents hydrogen, alkyl with 1–4 carbon atoms, phenyl or pyridyl, or a pharmacologically acceptable addition salt thereof.

2. A dihydropyrimidine according to claim 1, wherein such dihydropyrimidine is ethyl 6-methyl-4-(2-nitrophenyl)-2-phenyl-1,4-(dihydropyrimidine-5-carboxylate of the formula

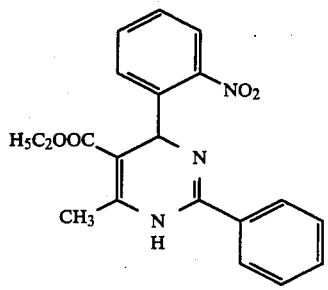

or a pharmacologically acceptable addition salt thereof.

3. A dihydropyrimidine according to claim 1, wherein such dihydropyrimidine is methyl 2,6-dimethyl-4-(3-nitrophenyl)-1,4-dihydropyrimidine-5-carboxylate of the formula

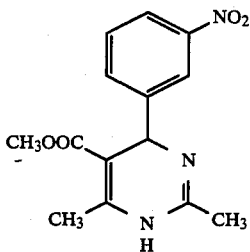

or a pharmacologically acceptable addition salt thereof.

4. A dihydropyrimidine according to claim 1, wherein such dihydropyrimidine is ethyl 6-methyl-4-[2-(4-methylbenzyloxy)-phenyl]-2-phenyl-1,4-dihydropyrimidine-5-carboxylate of the formula

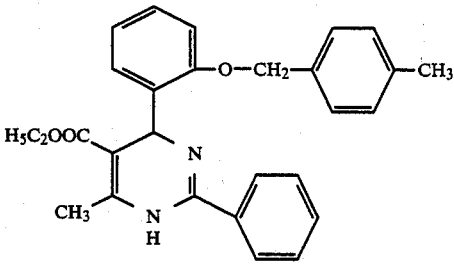

or a pharmacologically acceptable addition salt thereof.

5. A dihydropyrimidine according to claim 1, wherein such dihydropyrimidine is methyl 2,6-dimethyl-4-(4-[3-chlorophenyl]-3-nitro-phenyl)-1,4-dihydropyrimidine-5-carboxylate of the formula

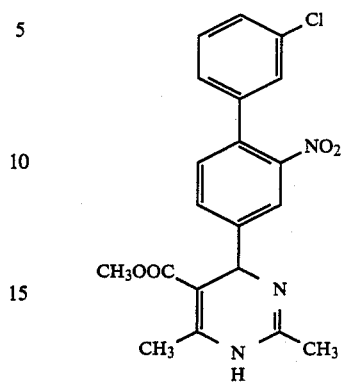

or a pharmacologically acceptable addition salt thereof.

6. A dihydropyrimidine according to claim 1, wherein such dihydropyrimidine is methyl 2-methyl-6-phenyl-4-(2-trifluoromethyl-phenyl)-1,4-dihydropyrimidine-5-carboxylate of the formula

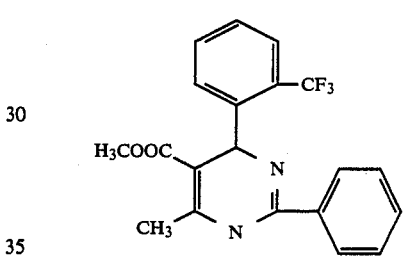

or a pharmacologically acceptable addition salt thereof.

7. A circulation-active composition comprising a circulation-affecting effective amount of a dihydropyrimidine or salt thereof according to claim 1 in admixture with a diluent.

8. A unit dose of a composition according to claim 7 in the form of a tablet, capsule or ampule.

9. A method of affecting the circulation of a patient which comprises administering to such patient a circulation-affecting effective amount of a dihydropyrimidine or salt thereof according to claim 1.

10. The method according to claim 9, wherein such dihydropyrimidine is
ethyl 6-methyl-4-(2-nitrophenyl)-2-phenyl-1,4-dihydropyrimidine-5-carboxylate,
methyl 2,6-dimethyl-4-(3-nitrophenyl)-1,4-dihydropyrimidine-5-carboxylate,
ethyl 6-methyl-4-[2-(4-methylbenzyloxy)-phenyl]-2-phenyl-1,4-dihydropyrimidine-5-carboxylate,
methyl 2,6-dimethyl-4-(4-[3-chlorophenyl]-3-nitrophenyl)-1,4-dihydropyrimidine-5-carboxylate or
methyl 2-methyl-6-phenyl-4-(2-trifluoromethyl-phenyl)-1,4-dihydropyrimidine-5-carboxylate,
or a pharmacologically acceptable addition salt thereof.

* * * * *